US011517183B2

(12) United States Patent
Meglan et al.

(10) Patent No.: US 11,517,183 B2
(45) Date of Patent: *Dec. 6, 2022

(54) SURGICAL SYSTEM FOR DETECTING GRADUAL CHANGES IN PERFUSION

(71) Applicant: Covidien LP, Mansfield, MA (US)

(72) Inventors: Dwight Meglan, Westwood, MA (US); Meir Rosenberg, Newton, MA (US)

(73) Assignee: COVIDIEN LP, Mansfield, MA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/143,243

(22) Filed: Jan. 7, 2021

(65) Prior Publication Data

US 2021/0145259 A1     May 20, 2021

Related U.S. Application Data

(63) Continuation of application No. 15/768,150, filed as application No. PCT/US2016/057797 on Oct. 20, 2016, now Pat. No. 10,912,449.

(Continued)

(51) Int. Cl.
*A61B 1/00*     (2006.01)
*A61B 1/005*     (2006.01)
(Continued)

(52) U.S. Cl.
CPC .......... *A61B 1/00186* (2013.01); *A61B 1/005* (2013.01); *A61B 1/00009* (2013.01);
(Continued)

(58) Field of Classification Search
CPC . A61B 1/00186; A61B 1/00096; A61B 1/005; A61B 1/0676; A61B 1/07; A61B 1/00009; A61B 1/0669; A61B 1/05; A61B 90/361; A61B 2090/365; A61B 5/7289; A61B 5/318; A61B 34/35
See application file for complete search history.

(56) References Cited

U.S. PATENT DOCUMENTS 6,132,368 A    10/2000   Cooper
6,206,903 B1    3/2001   Ramans
(Continued)

OTHER PUBLICATIONS

Extended European Search Report dated Jun. 14, 2021 corresponding to counterpart Patent Application EP 21172585.8.
(Continued)

*Primary Examiner* — Wayne H Cai (57) ABSTRACT

The present disclosure is directed to an augmented reality surgical system. The system includes an endoscope that captures an image of the region of interest of a patient and an ECG device that records an ECG of the patient. A controller receives the image and applies at least one image processing filter to the image. The image processing filter includes a decomposition filter that decomposes the image into frequency bands. A temporal filter is applied to the frequency bands to generate temporally filtered bands. An adder adds each band frequency band to a corresponding temporally filtered band to generate augmented bands. A reconstruction filter generates an augmented image by collapsing the augmented bands. The controller also receives the ECG and processes the augmented image with the ECG to generate an ECG filtered augmented image. A display displays the ECG filtered augmented image to a user.

20 Claims, 5 Drawing Sheets

Related U.S. Application Data (60) Provisional application No. 62/245,526, filed on Oct. 23, 2015.

(51) Int. Cl.

| | | |
|---|---|---|
| *A61B 1/05* | (2006.01) | |
| *A61B 1/06* | (2006.01) | |
| *A61B 1/07* | (2006.01) | |
| *A61B 5/00* | (2006.01) | |
| *A61B 5/318* | (2021.01) | |
| *A61B 90/00* | (2016.01) | |
| *A61B 34/35* | (2016.01) | |

(52) U.S. Cl.
CPC ............ *A61B 1/00096* (2013.01); *A61B 1/05* (2013.01); *A61B 1/0669* (2013.01); *A61B 1/0676* (2013.01); *A61B 1/07* (2013.01); *A61B 5/318* (2021.01); *A61B 5/7289* (2013.01); *A61B 90/361* (2016.02); *A61B 34/35* (2016.02); *A61B 2090/365* (2016.02)

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,558,618 B1 | 7/2009 | Williams |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,239,170 B2 | 8/2012 | Wegerich |
| 8,256,319 B2 | 9/2012 | Cooper et al. |
| 8,271,071 B2 | 9/2012 | Maruccio |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |

(56) References Cited

U.S. PATENT DOCUMENTS

| | | |
|---|---|---|
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,696,685 B2 | 4/2014 | Gilboa |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |

(56) References Cited

U.S. PATENT DOCUMENTS

| | | |
|---|---|---|
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,449 B2 | 2/2021 | Meglan et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 2007/0055128 A1 | 3/2007 | Glossop |
| 2010/0158330 A1 | 6/2010 | Guissin |
| 2013/0035581 A1 | 2/2013 | Vesto |
| 2013/0038707 A1 | 2/2013 | Cunningham et al. |
| 2014/0213849 A1 | 7/2014 | Pandey |
| 2014/0275760 A1 | 9/2014 | Lee et al. |
| 2015/0257653 A1 | 9/2015 | Hyde |
| 2017/0202633 A1 | 7/2017 | Liu |

OTHER PUBLICATIONS

European Office Action dated Mar. 6, 2020 corresponding to counterpart Patent Application EP 16858177.5.

International Search Report and Written Opinion of Int'l Appln. PCT/US16/057797 dated Feb. 1, 2017.

Extended European Search Report dated May 23, 2019 corresponding to counterpart Patent Application EP 16858177.5.

SURGICAL SYSTEM FOR DETECTING GRADUAL CHANGES IN PERFUSION

CROSS-REFERENCE TO RELATED APPLICATIONS

This application is a Continuation Application claiming the benefit of and priority to U.S. patent application Ser. No. 15/768,150, filed Apr. 13, 2018, which is a U.S. National Stage Application filed under 35 U.S.C. § 371(a) of International Patent Application Serial No. PCT/US2016/057797, filed Oct. 20, 2016, which claims the benefit of and priority to U.S. Provisional Patent Application Ser. No. 62/245,526, filed Oct. 23, 2015, the entire disclosure of which is incorporated by reference herein.

Minimally invasive surgeries have involved the use of multiple small incisions to perform a surgical procedure instead of one larger opening. The small incisions have reduced patient discomfort and improved recovery times. The small incisions have also limited the visibility of internal organs, tissue, and other matter.

Endoscopes have been inserted in one or more of the incisions to make it easier for clinicians to see internal organs, tissue, and other matter inside the body during surgery. These endoscopes have included a camera with an optical and/or digital zoom capability that is coupled to a display showing the magnified view of organs, tissue, and matter inside the body as captured by the camera. Existing endoscopes and displays, especially those used in surgical robotic systems, have had a limited ability to identify conditions or objects that are within the field of view of the camera but are not fully visible within the spectrum shown on the display. For example, existing minimally invasive and robotic surgical tools, including but not limited to endoscopes and displays, have had a limited, if any, ability to identify blood perfusion during a minimally invasive surgical procedure. In order to identify blood perfusion, many procedures involved adding taggants to the patient's blood stream.

In view thereof, there is a need for identifying a greater range of possible conditions or objects that are within the field of view of a surgical camera but are not fully visible within the spectrum shown on the display during surgery.

SUMMARY

The present disclosure relates to video imaging techniques of target surgical sites, in vivo, during a surgical procedure, for detecting gradual changes in perfusion of tissue at the target surgical site.

In an aspect of the present disclosure, an augmented reality surgical system is provided. The system includes an endoscope configured to capture an image of a region of interest of a patient and an electrocardiogram (ECG) device configured to record electrical activity of a heart of the patient. The system also includes a controller configured to receive the image and apply at least one image processing filter to the image to generate an augmented image. The image processing filter includes a decomposition filter configured to decompose the image into a plurality of frequency bands, a temporal filter that is configured to be applied to the plurality of frequency bands to generate a plurality of temporally filtered bands, an adder configured to add each band in the plurality of frequency bands to a corresponding band in the plurality of temporally filtered bands to generate a plurality of augmented bands, a reconstruction filter configured to generate an augmented image by collapsing the plurality of augmented bands, and an ECG filter configured to generate the ECG filtered augmented image based on the augmented image and the electrical activity. The ECG filtered augmented image of the patient is then displayed to a user.

The image capture device may capture a video having a plurality of image frames and the controller applies the at least one image processing filter to each image frame of the plurality of image frames.

The temporal filter isolates at least one frequency band from the plurality of frequency bands to generate the plurality of temporally filtered bands. The plurality of temporally filtered bands are amplified by an amplifier before each band in the plurality of frequency bands is added to a corresponding band in the plurality of temporally filtered bands to generate a plurality of augmented bands.

The ECG filter may generate a baseline time varying signal. The ECG filter may average the baseline time varying amplified color and remove the averaged baseline time varying amplified color from the augmented image.

In some aspects, the endoscope includes an illumination device or optical fiber light guide. The endoscope may emit light having a wavelength that is selectively absorbed or reflected by arterial blood and/or venous blood.

In another aspect of the present disclosure, a method for generating an electrocardiogram (ECG) filtered augmented image is provided. The method includes capturing at least one image using an endoscope and recording electrical activity of a heart of the patient using an ECG device. The at least one image is decomposed to generate a plurality of frequency bands. A temporal filter is applied to the plurality of frequency bands to generate a plurality of temporally filtered bands. Each band in the plurality of frequency bands is added to a corresponding band in the plurality of temporally filtered bands to generate a plurality of augmented bands. The plurality of augmented bands is collapsed to generate an augmented image. The augmented image and the electrical activity are used to generate the ECG filtered augmented image which is displayed on a display.

At least one frequency band is isolated from the plurality of frequency bands. The temporally filtered bands may be amplified before adding each band in the plurality of frequency bands to a corresponding band in the plurality of temporally filtered bands to generate a plurality of augmented bands.

A baseline time varying amplified color is generated which may then be averaged. The averaged baseline time varying amplified color is removed from the augmented image to generate the ECG filtered augmented image.

In some aspects, light having a wavelength that is selectively absorbed or reflected by arterial blood or venous blood is emitted onto the tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Image data captured from a surgical camera during a surgical procedure may be analyzed to identify additional not readily human perceivable properties of objects within the camera field of view that may not be apparent to people viewing the camera image displayed on a screen. Various image processing technologies may be applied to this image data to identify different conditions in the patient. For example, Eulerian image amplification techniques may be used to identify small wavelength or "color" changes of light in different parts of a captured image. These changes may be further analyzed to identify re-perfusion, arterial flow, and/or vessel types.

Eulerian image amplification may also be used to make motion or movement between image frames more visible to a clinician. In some instances changes in a measured intensity of predetermined wavelengths of light between different image frames may be presented to a clinician to make the clinician more aware of the motion of particular objects of interest (such as blood).

Hyper-spectral image analysis may be used to identify subtle changes in small areas within the range of view that may be invisible or otherwise difficult for the human eye to discern. These hyper-spectral image analysis techniques may be combined with Eulerian image amplification to identify a specific set of changes in these areas.

One or more of Eulerian image amplification, image algebra, hyper-spectral image analysis, and filtering technologies may be included as part of an imaging system. These technologies may enable the imaging system to provide additional information about unapparent conditions and objects within a camera's field of view and enhance surgical outcomes. This additional information may include, but is not limited to, identifying tissue perfusion, locating arteries of specific sizes (such as larger arteries), verifying an effectiveness of vessel sealing, identifying a heat signature of abnormal tissue, verifying desired object motion (such as a lack of movement in edges of dead tissue or verifying proper flow after resection), distinguishing between similar looking objects (such as between the ureter, inferior mesenteric artery, and/or surrounding blood), and detecting small leaks (such as leaks that may occur after an anastomosis).

One or more of these technologies may be included as part of an imaging system in a surgical robotic system to provide a clinician with additional information in real time about unapparent conditions and objects within an endoscope's field of view. This may enable the clinician to quickly identify, avoid, and/or correct undesirable situations and conditions during surgery. For example, a clinician may be able to verify during surgery that vessels have been properly sealed, that blood is properly flowing, that there are no air leaks after an anastomosis, and/or that diseased tissue has been removed. The clinician may then be able to correct these issues if needed during the surgery. A clinician may also be able to identify delicate or critical objects in the body that the surgical instruments should avoid contacting or handle with extra care, such as larger arteries or the ureter.

Meanwhile, an electrocardiogram (ECG) device is generally used to measure the electrical activity of a patient's heart. The electrical activity corresponds to the cyclic change of blood flow through the body. There is a consistent correlation between the electrical activity and the variation in blood flow at a target region.

The present disclosure is directed to systems and methods for providing an augmented image in real time to a clinician during a surgical procedure. The systems and methods described herein apply image processing filters to a captured image to provide an augmented or enhanced image to a clinician via a display. In some embodiments, the systems and methods permit video capture during a surgical procedure. The captured video is processed in real time or near real time and then displayed to the clinician as an augmented image. The image processing filters are applied to each frame of the captured video. Providing the augmented image or video to the clinician permits the clinician to identify and address potential adverse physiologic conditions thereby reducing the need for additional surgical procedures as well as ensuring the effectiveness of the original surgical procedure.

The embodiments described herein enable a clinician to identify and filter out the cyclical change in blood flow, i.e., resulting from the propagation of flow from the heart, in the augmented image to permit a clinician to determine if there is an abnormal change in blood perfusion. The clinician may also determine if the change in blood perfusion is within the arterial blood flow or the venous blood flow. The embodiments described herein use a concept known as ECG gating in which data is acquired in relation to the ECG identified cardiac cycle. Using ECG gating to time average the color amplification of a region of interest, permits subtle changes in tissue to be readily and immediately observed without adding taggants or making modifications to existing endoscopes. The systems described herein permit clinicians to see and understand clinically significant situations such as blood flow obstructions from clamping of tissue.

Figure 1:
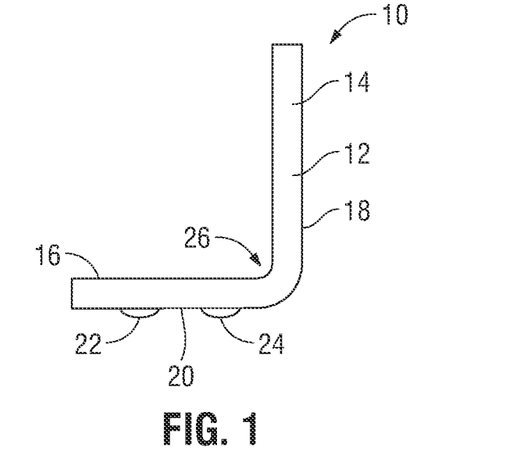
FIG. 1 is a schematic side view of an endoscope in accordance with embodiments of the present disclosure.

Turning to FIG. 1, an endoscope 10 according to an embodiment of the present disclosure is illustrated. An example of endoscope 10 can be found in U.S. patent application Ser. No. 14/150,443 filed on Jan. 8, 2014, the contents of which are hereby incorporated by reference. The endoscope 10 includes an elongated shaft 12 having a proximal portion 14 and a distal portion 16. In one embodiment, the elongated shaft 12 is made from shape-memory alloy (e.g. Nitinol) such that the elongate shaft 12 may have a straight or linear cylindrical configuration in a relaxed state (i.e., in the absence of externally applied forces). In the linear configuration, the distal portion 16 of the endoscope 10 is inserted into a conventional trocar sleeve or cannula (not shown), which is essentially a straight, hollow instrument that allows the endoscope 10 to be inserted into the abdominal cavity of a patient. The cannula and/or endoscope 10 may be supported on the arm of a robotic surgical system. The cannula is typical of known cannulas in the art and is made from polyvinyl chloride (PVC) or any other flexible material suitable for use in the abdominal cavity or other medical applications.

Prior to insertion of the elongated shaft 12 into the cannula and the abdominal cavity, the surgeon adjusts the elongated shaft 12 into a pre-bent configuration to obtain an optimal viewing window. The elongated shaft 12 is then returned to the original straight configuration. Once inserted into the abdominal cavity, the elongated shaft assumes the pre-bent configuration. In one embodiment, the elongated shaft 12 assumes the pre-bent configuration in response to temperature within the body cavity. In an alternate embodiment, the elongated shaft 12 responds to an electrical signal from a control unit.

With continued reference to FIG. 1, the proximal and distal portions 14, 16 of the elongated shaft 12 each have an outer surface 18, 20, respectively. The outer surface 20 of the distal portion 16 includes at least one image capturing device 22 thereon. The image capturing device 22 allows the surgeon to clearly view the inside of the abdominal cavity. Preferably, the image capturing device 22 is a low profile camera so that the image capturing device 22 does not obstruct the surgeon's tools during the procedure. At least one illumination device 24 is disposed adjacent the image capturing device 22 to illuminate the inside of the abdominal cavity and aide in viewing the internal organs with the image capturing device 22.

The image capturing device 22 and illumination device 24 can be disposed in varying configurations along the distal portion 16 of the elongated shaft 12. Based on the location of the image capturing device 22, the elongated shaft 12 is pre-bent to provide the desired location as well as optimal angle for the surgeon. This variation in the pre-bent configuration is determined by varying the length of the bent portion (i.e. the distal portion) and the angle of the bend 26. FIG. 1 illustrates the angle of the bend 26 as a generally ninety degree angle with the distal portion 16 being generally the same length as the proximal portion 14, however, it is understood that any bend angle to allow the surgeon to view the body cavity can be achieved. Further, FIG. 1 illustrates the image capturing device 22 and the illumination device 24 generally along the same longitudinal axis with the image capturing device 22 being near a distal end of the elongated shaft 12. It will be appreciated that this configuration can be altered during manufacturing based on the particular needs of the surgical procedure.

Figure 2A:
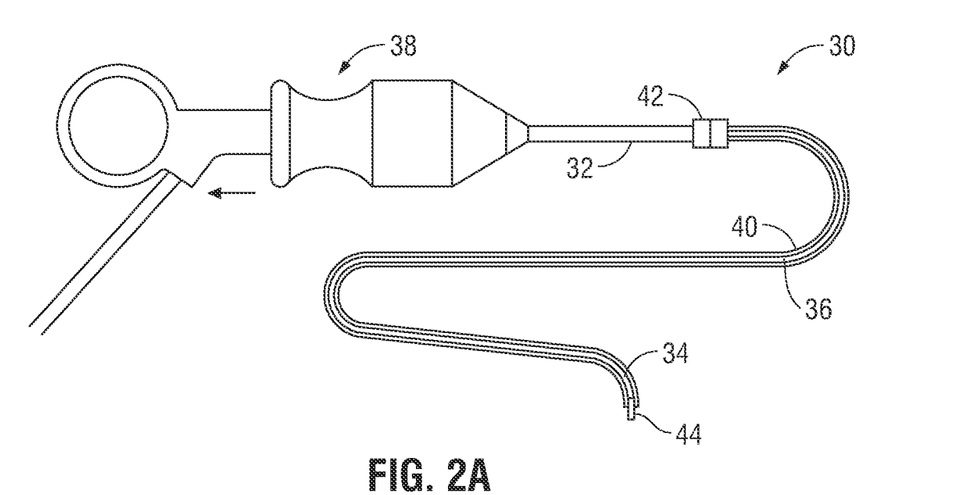
FIG. 2A is a schematic side view of a steerable endoscope in accordance with embodiments of the present disclosure.

Turning to FIG. 2A, an endoscope in accordance with another embodiment of the present disclosure is shown generally as 30. Endoscope 30 includes a locatable guide 32 which has a steerable distal tip 34, a flexible body 36 and, at its proximal end, a control handle or housing 38. Guide 32 may be inserted into a sheath 40 and may be locked in position by a locking mechanism 42 or any other connectors. A position sensor element 44 is integrated with distal tip 34 and allows monitoring of the tip position and orientation (6 degrees of freedom) relative to a reference coordinate system. An example of endoscope 30 can be found in U.S. patent application Ser. No. 12/723,577 filed on Mar. 12, 2010 (now U.S. Pat. No. 8,696,685), the contents of which are hereby incorporated by reference.

Figure 2B:
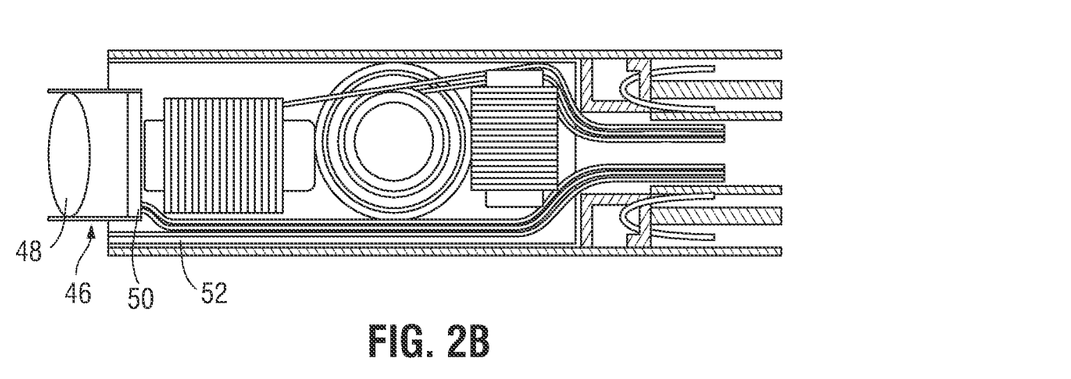
FIG. 2B is a cross sectional view of a distal end of the endoscope of FIG. 2A.

Turning now to FIG. 2B, distal tip 34 of endoscope 30 includes an image sensor 46. By way of example, image sensor 46 is shown here as an optical imaging sensor with a lens 48 positioned in front of an image sensor array 50. Illumination is provided via an optic fiber light guide 52.

The illumination device 24 of FIG. 1 and the optical fiber light guide 32 may emit specific light frequencies that may be used to illuminate a surgical site to selectively enhance the visibility or arterial and venous blood flow.

Figure 3:
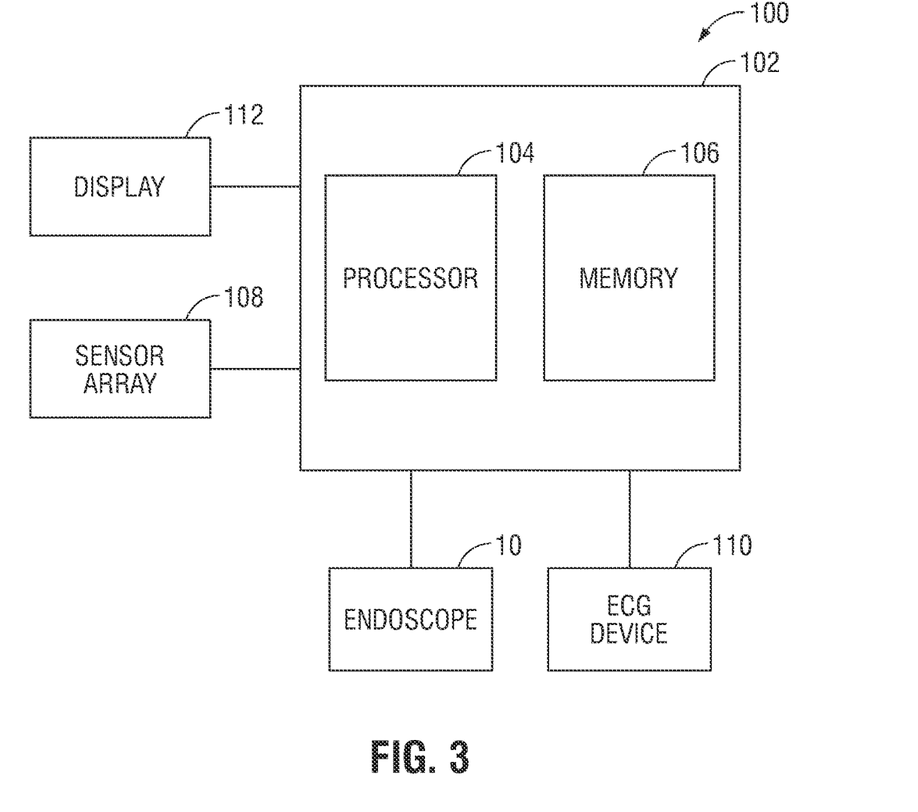
FIG. 3 is a block diagram of a system for augmenting an image or video in accordance with an embodiment of the present disclosure.

Turning to FIG. 3, a system for augmenting a surgical environment, according to embodiments of the present disclosure, is shown generally as 100. System 100 includes a controller 102 that has a processor 104 and a memory 106. The system 100 receives images from endoscope 10 or endoscope 30.

A sensor array 108 of system 100 provides information concerning the surgical environment to the controller 102. For instance, sensor array 108 includes biometric sensors capable of obtaining biometric data of a patient such as, pulse, temperature, blood pressure, blood oxygen levels, heart rhythm, etc. Sensor array 108 may also include hyper-spectral sensors to perform hyper-spectral imaging. Sensor array 108 may be incorporated in endoscope 10 or endoscope 30 or sensor array 108 may be provided as a separate standalone unit.

An ECG device 110 of system 100 provides an ECG or electrical activity signals of the heart of the patient to the controller 102. A display 112 of system 100, displays augmented images to a clinician during a surgical procedure. In some embodiments, the controller 102 may communicate with a central server (not shown) via a wireless or wired connection. The central server may store images of a patient or multiple patients that may be obtained using x-ray, a computed tomography scan, or magnetic resonance imaging.

Figure 4:
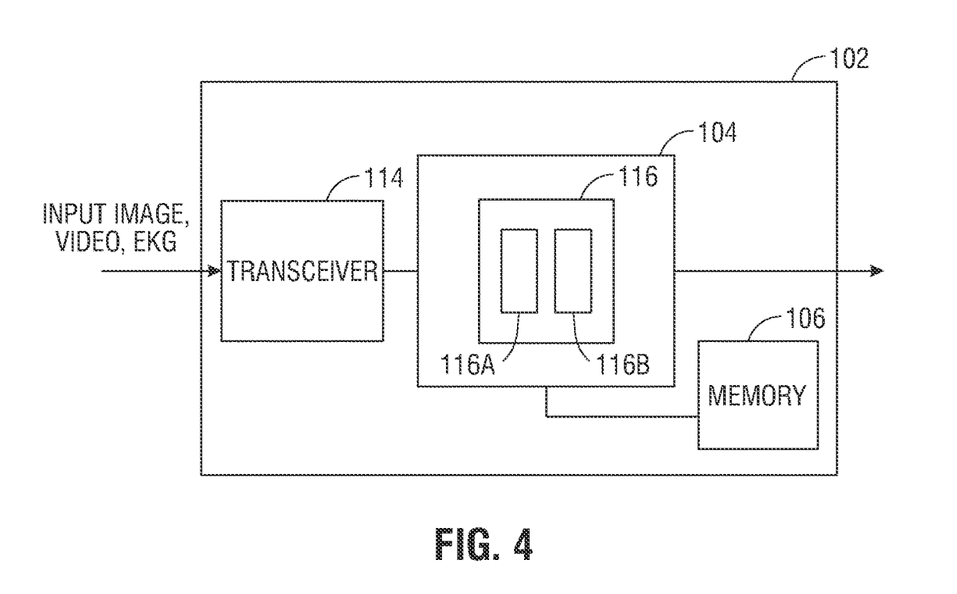
FIG. 4 is a system block diagram of a controller of FIG. 3.

FIG. 4 depicts a system block diagram of the controller 102. As shown in FIG. 4, the controller 102 includes a transceiver 114 configured to receive still frame images or video from endoscope 10, data from sensor array 110, or ECG data or signals from the ECG device 110. In some embodiments, the transceiver 114 may include an antenna to receive the still frame images, video, data, or ECG data or signals via a wireless communication protocol. The still frame images, video, data, or ECG data or signals are provided to the processor 104. The processor 104 includes an image processing filter 116 that processes the received still frame images, video, data, or ECG data or signals to generate an augmented image or video. The image processing filter 116 may be implemented using discrete components, software, or a combination thereof. The augmented image or video is provided to the display 112.

Figure 5:
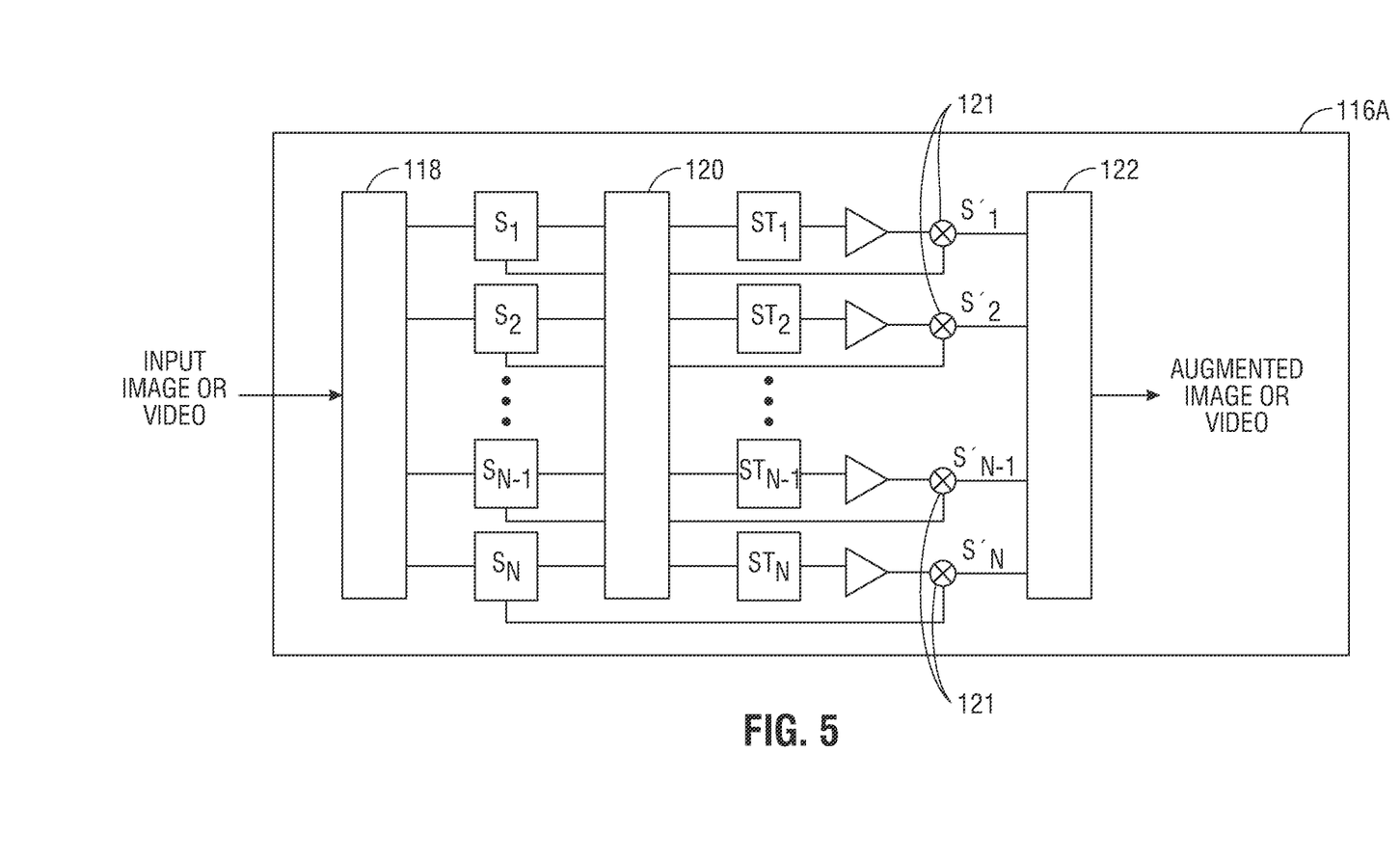
FIG. 5 is a system block diagram of a sub assembly of an image processing filter of FIG. 4.

Turning to FIG. 5, a system block diagram of an image processing filter that may be applied to video received by transceiver 114 is shown as 116A. In the image processing filter 116A, each frame of a received video is decomposed into different frequency bands $S_1$ to $S_N$ using a decomposition filter 118. The decomposition filter 118 uses an image processing technique known as a pyramid in which an image is subjected to repeated smoothing and subsampling.

After the frame is subjected to the decomposition filter 118, a temporal filter 120 is applied to all the frequency bands $S_1$ to Sato generate temporally filtered bands $ST_1$ to $ST_N$. The temporal filter 120 is a bandpass filter that is used to extract one or more desired frequency bands. For example, if the clinician knows the patient's pulse, the clinician can set the bandpass frequency of the temporal filter 120, using a user interface (not shown), to magnify the frequency band that corresponds to the patient's pulse. In other words, the bandpass filter is set to a narrow range that includes the patient's pulse and applied to all the frequency bands $S_1$ to $S_N$. Only the frequency band that corresponds to the set range of the bandpass filter will be isolated or passed through. In an embodiment, the bandpass frequency of the temporal filter 120 may be set automatically by system 100 based on the patient's pulse being measured by a pulse sensor, included in sensor array 108, and transmitted to temporal filter 120.

All of the temporally filtered bands $ST_1$ to $ST_N$ are individually amplified by an amplifier having a gain "α".

Because the temporal filter 120 isolates or passes through a desired frequency band of bands $S_1$ to $S_N$, only the desired frequency band of bands $S_1$ to $S_N$ gets amplified. The amplified temporally filtered bands $ST_1$ to $ST_N$ are then added, by adder 121, to the original frequency bands $S_1$ to $S_N$ to generate augmented bands $S'_1$ to $S'_N$. Each frame of the video is then reconstructed using a reconstruction filter 122 by collapsing augmented bands $S'_1$ to $S'_N$ to generate an augmented frame. All the augmented frames are combined to produce the augmented video. The augmented video that is shown to the clinician includes a portion that is magnified, i.e., the portion that corresponds to the desired frequency band, to enable the clinician to easily identify such portion.

In some embodiments, instead of using an amplifier to amplify the isolated temporally filtered band, the image processing filter 116A may highlight the temporally filtered band using one or more colors before reconstructing the video. Using an enhanced color for a desired portion of the patient, e.g., a vessel or nerve, may make it easier for the clinician to identify the location of such portion.

Figure 6:
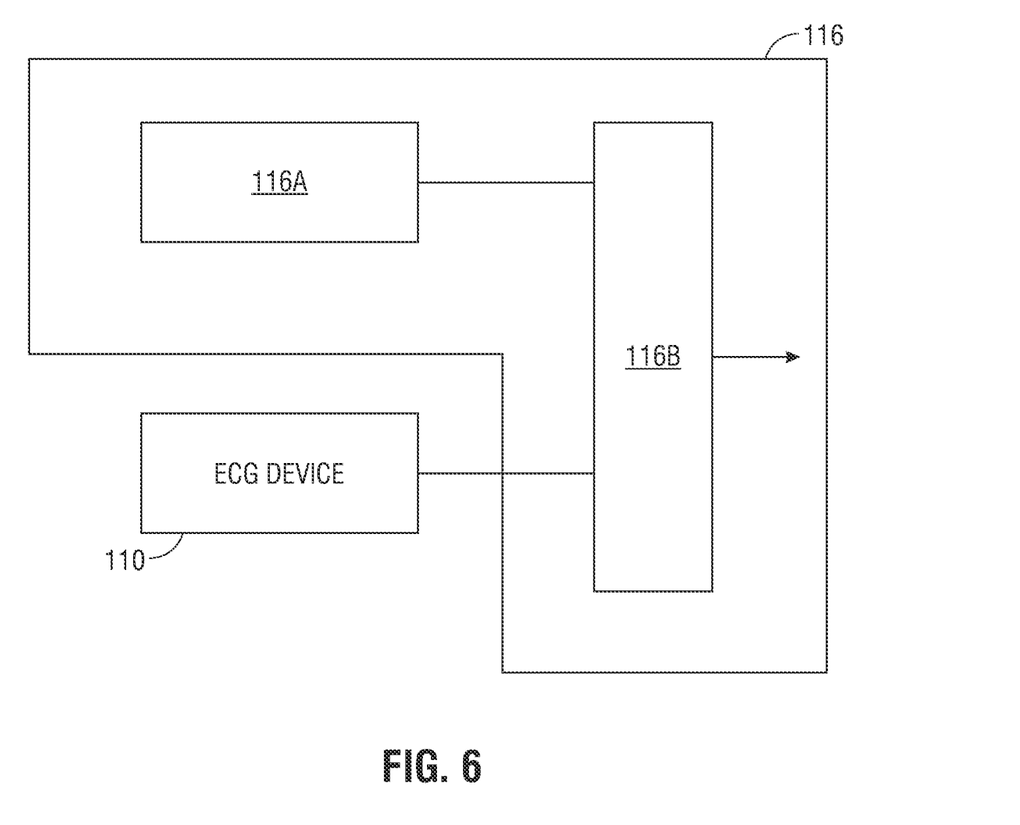
FIG. 6 is a system block diagram of the image processing filter of FIG. 4.

Turning to FIG. 6, image processing filter 116A feeds the augmented video to ECG filter 116B. ECG filter 116B also receives ECG data or signals that were obtained by ECG device 110. Because the ECG data or signals is correlated with a cyclic change in blood flow, there is a consistent offset between the ECG data or signals and variation in blood flow at the surgical site. By using the consistent offset, the ECG filter 116B may determine a baseline time varying signal using the QRS signal pattern observed in the ECG data or signals. The ECG filter 116B then averages the baseline time varying signal and removes the average signal from the augmented video to generate an ECG filtered augmented video. In the ECG filtered augmented video, only unique changes in blood flow are visible, thus permitting a surgeon to view situations in real time, e.g., cessation in blood flow from over clamping tissue using jaw like end effector.

The image processing performed by image processing filter 116 may be combined with the specific light wavelengths emitted by illumination device 24 or optical fiber light guide 52, e.g., 660 nm and 940 nm, to determine if there is an abnormal blood flow in the arterial system or the venous system. Specifically, the illumination device 24 or optical fiber light guide 52 may emit light having a wavelength that selectively is absorbed or reflected by arterial blood. The received images and the ECG data or signals are processed by the image processing filter 116 to check for abnormalities in the arterial blood flow. The same procedure would apply to venous blood except that the illumination device 24 or optical fiber light guide 52 would emit light having a wavelength that isolates venous blood.

The above-described embodiments may also be configured to work with robotic surgical systems and what is commonly referred to as "Telerobotic surgery." Such systems employ various robotic elements to assist the clinician in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include, remotely steerable systems, flexible surgical systems, remotely flexible surgical systems, remotely articulating surgical systems, wireless surgical systems, modular or selectively configurable remotely operated surgical systems, etc.

Figure 7:
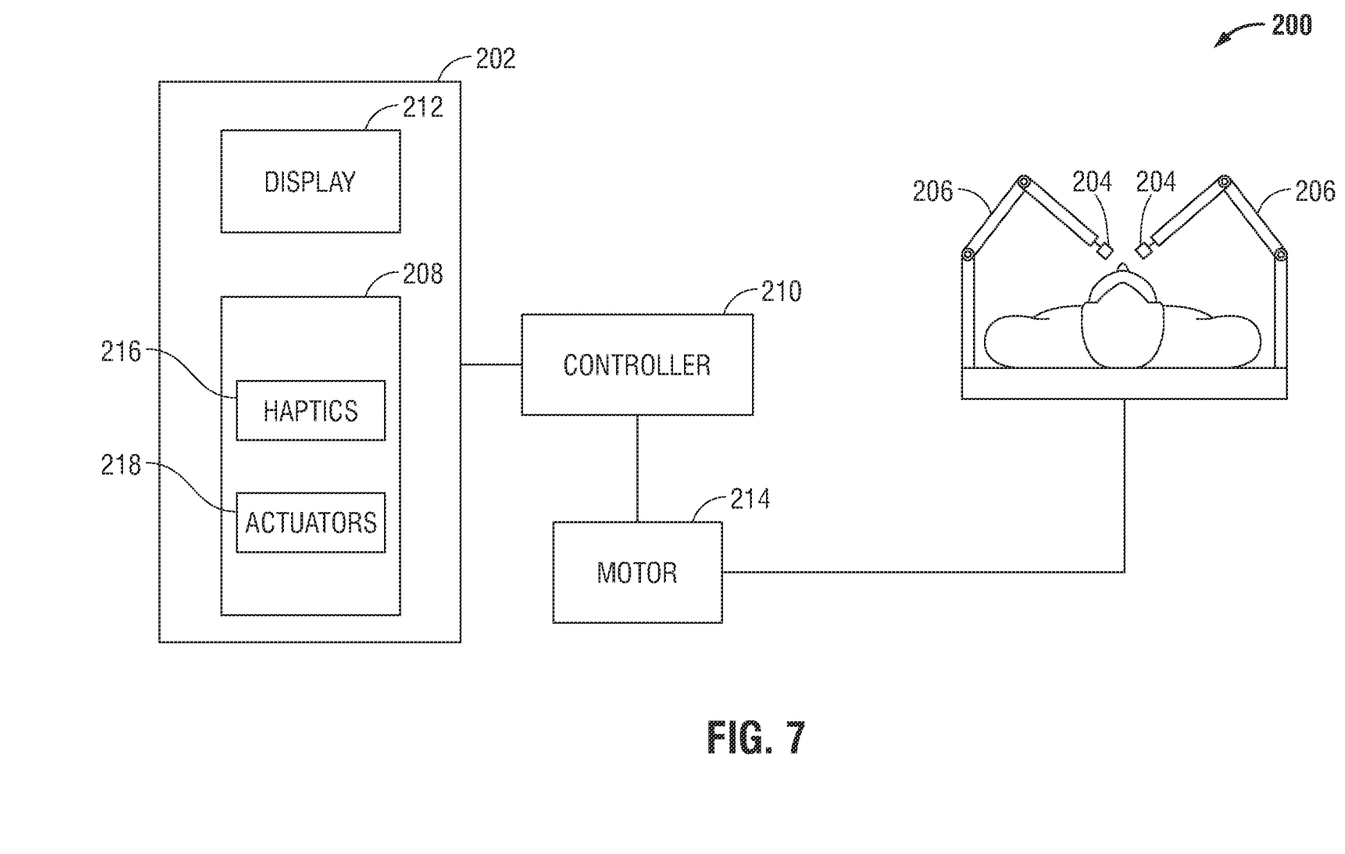
FIG. 7 is a system block diagram of a robotic surgical system in accordance with an embodiment of the present disclosure.

As shown in FIG. 7, a robotic surgical system 200 may be employed with one or more consoles 202 that are next to the operating theater or located in a remote location. In this instance, one team of clinicians or nurses may prep the patient for surgery and configure the robotic surgical system 200 with one or more instruments 204 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 206 of the surgical system 200 are typically coupled to a pair of master handles 208 by a controller 210. Controller 210 may be integrated with the console 202 or provided as a standalone device within the operating theater. The handles 206 can be moved by the clinician to produce a corresponding movement of the working ends of any type of surgical instrument 204 (e.g., probe, end effectors, graspers, knifes, scissors, etc.) attached to the robotic arms 206. For example, surgical instrument 204 may be a probe, e.g., endoscope, that includes an image capture device. The probe is inserted into a patient in order to capture an image of a region of interest inside the patient during a surgical procedure. One or more of the image processing filters 116A or 116B are applied to the captured image by the controller 210 before the image is displayed to the clinician on a display 212.

The movement of the master handles 208 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 204.

During operation of the surgical system 200, the master handles 208 are operated by a clinician to produce a corresponding movement of the robotic arms 206 and/or surgical instruments 204. The master handles 208 provide a signal to the controller 208 which then provides a corresponding signal to one or more drive motors 214. The one or more drive motors 214 are coupled to the robotic arms 206 in order to move the robotic arms 206 and/or surgical instruments 204.

The master handles 208 may include various haptics 216 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 216 provide the clinician with enhanced tactile feedback simulating actual operating conditions. The haptics 216 may include vibratory motors, electroactive polymers, piezoelectric devices, electrostatic devices, subsonic audio wave surface actuation devices, reverse-electrovibration, or any other device capable of providing a tactile feedback to a user. The master handles 208 may also include a variety of different actuators 218 for delicate tissue manipulation or treatment further enhancing the clinician's ability to mimic actual operating conditions.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refers to a clinician or any medical professional, such as a doctor, nurse, technician, medical assistant, or the like) performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C #, C++, Delphi, Fortran, Java, JavaScript, Machine code, operating system command languages, Pascal, Perl, PL1, Python, scripting languages, Visual Basic, metalanguages which themselves specify programs, and all first, second, third, fourth, and fifth generation computer languages. Also included are database and other data schemas, and any other meta-languages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An augmented reality surgical system comprising:
an image capture device configured to capture an image of a region of interest of a patient;
an electrocardiogram (ECG) device configured to record electrical activity of a heart of the patient; and
a controller configured to receive the image and apply at least one image processing filter to the image to generate an ECG filtered augmented image, the image processing filter including:
a decomposition filter configured to decompose the image into a plurality of frequency bands;
a temporal filter configured to be applied to the plurality of frequency bands to generate a plurality of temporally filtered bands;
an adder configured to add each band in the plurality of frequency bands to a corresponding band in the plurality of temporally filtered bands to generate a plurality of augmented bands;
a reconstruction filter configured to generate an augmented image by collapsing the plurality of augmented bands; and
an ECG filter configured to generate the ECG filtered augmented image based on the augmented image and the electrical activity.

2. The augmented reality surgical system of claim 1, further comprising:
a display configured to display the ECG filtered augmented image of the patient to a user during the surgical procedure.

3. The augmented reality surgical system of claim 1, wherein the image capture device captures a video having a plurality of image frames and the controller applies the at least one image processing filter to each image frame of the plurality of image frames.

4. The augmented reality surgical system of claim 1, wherein the temporal filter includes a bandpass filter.

5. The augmented reality surgical system of claim 4, wherein a bandpass frequency of the bandpass filter is set by a clinician.

6. The augmented reality surgical system of claim 1, wherein the temporal filter isolates at least one frequency band from the plurality of frequency bands to generate the plurality of temporally filtered bands.

7. The augmented reality surgical system of claim 1, wherein the plurality of temporally filtered bands are amplified by an amplifier before each band in the plurality of frequency bands is added to the corresponding band in the plurality of temporally filtered bands to generate the plurality of augmented bands.

8. The augmented reality surgical system of claim 1, wherein the ECG filter generates a baseline time varying signal.

9. The augmented reality surgical system of claim 8, wherein the ECG filter averages the baseline time varying amplified color and removes the averaged baseline time varying amplified color from the augmented image.

10. The augmented reality surgical system of claim 1, wherein the image capture device includes an illumination device or an optical fiber light guide.

11. The augmented reality surgical system of claim 1, wherein the image capture device emits light having a wavelength that selectively is absorbed or reflected by arterial blood.

12. The augmented reality surgical system of claim 1, wherein the image capture device emits light having a wavelength that selectively is absorbed or reflected by venous blood.

13. A method for generating an electrocardiogram (ECG) filtered augmented image of a region of interest of a patient during a surgical procedure, the method comprising:
- capturing at least one image of the region of interest using an image capture device;
- recording electrical activity of a heart of the patient using an ECG device;
- decomposing the at least one image to generate a plurality of frequency bands;
- applying a temporal filter to the plurality of frequency bands to generate a plurality of temporally filtered bands;
- adding each band in the plurality of frequency bands to a corresponding band in the plurality of temporally filtered bands to generate a plurality of augmented bands;
- collapsing the plurality of augmented bands to generate an augmented image; and
- generating the ECG filtered augmented image based on the augmented image and the electrical activity.

14. The method of claim 13, further comprising displaying the ECG filtered augmented image on a display.

15. The method of claim 13, further comprising isolating at least one frequency band from the plurality of frequency bands.

16. The method of claim 15, further comprising amplifying the temporally filtered bands, before adding each band in the plurality of frequency bands to a corresponding band in the plurality of temporally filtered bands, to generate a plurality of augmented bands.

17. The method of claim 13, further comprising generating a baseline time varying amplified color.

18. The method of claim 17, further comprising:
- averaging the baseline time varying amplified color; and
- removing the averaged baseline time varying amplified color from the augmented image to generate the ECG filtered augmented image.

19. The method of claim 13, further comprising emitting light onto the target tissue having a wavelength that selectively is absorbed or reflected by arterial blood.

20. The method of claim 13, further comprising emitting light onto the target tissue having a wavelength that selectively is absorbed or reflected by venous blood.

* * * * *